United States Patent
Chen et al.

(10) Patent No.: US 11,040,105 B2
(45) Date of Patent: Jun. 22, 2021

(54) FILM-FORMING COMPOSITIONS FOR HARD CAPSULE SHELLS AND HARD CAPSULE SHELLS OBTAINED THEREOF

(71) Applicant: ROQUETTE FRERES, Lestrem (FR)

(72) Inventors: Armand Chen, Shanghai (CN); Yong Miao, Kunming (CN); Bernard Pora, Shanghai (CN)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 16/483,092

(22) PCT Filed: Feb. 7, 2018

(86) PCT No.: PCT/EP2018/053111
§ 371 (c)(1),
(2) Date: Aug. 2, 2019

(87) PCT Pub. No.: WO2018/146165
PCT Pub. Date: Aug. 16, 2018

(65) Prior Publication Data
US 2019/0351062 A1    Nov. 21, 2019

(30) Foreign Application Priority Data
Feb. 8, 2017   (EP) ..................... 17305147

(51) Int. Cl.
A61K 47/36    (2006.01)
A61K 9/48     (2006.01)
A61K 47/10    (2017.01)
A61K 47/26    (2006.01)

(52) U.S. Cl.
CPC ............ *A61K 47/36* (2013.01); *A61K 9/4816* (2013.01); *A61K 9/4833* (2013.01); *A61K 47/10* (2013.01); *A61K 47/26* (2013.01)

(58) Field of Classification Search
None
See application file for complete search history.

(56) References Cited

U.S. PATENT DOCUMENTS 6,375,981 B1    4/2002  Gilleland et al.
2012/0178858 A1  7/2012  Wnuk et al.

OTHER PUBLICATIONS

The International Search Report and Written Opinion, dated Apr. 20, 2018, in the corresponding PCT Appl. No. PCT/EP2018/053111.

*Primary Examiner* — Nannette Holloman

(57) ABSTRACT

The instant invention relates to film-forming compositions suitable for the manufacture of hard capsule shells, which are based on starchy material. The instant invention also relates hard capsule shells made from the film-forming compositions of the invention.

7 Claims, 2 Drawing Sheets

FILM-FORMING COMPOSITIONS FOR HARD CAPSULE SHELLS AND HARD CAPSULE SHELLS OBTAINED THEREOF

Cross-REFERENCE TO RELATED APPLICATIONS

This application is a National Stage Application of PCT/EP2018/053111 filed Feb. 7, 2018, which claims priority from European Patent Application No. 17305147.5, filed on Feb. 8, 2017. The priority of said PCT and European Patent Application are claimed. Each of the prior mentioned applications is hereby incorporated by reference herein in its entirety.

FIELD OF THE INVENTION

The instant invention relates to film-forming compositions suitable for the manufacture of hard capsule shells, which are based on starchy material. The instant invention also relates to hard capsule shells made from the film-forming compositions of the invention.

CONTEXT OF THE INVENTION

Hard capsules are solid dosage forms with hard shells, classically intended for oral administration, which usually contain one or more active ingredient(s) and one or more excipient(s).

Hard capsules have shells consisting of two prefabricated cylindrical sections that fit together. One end of each section is rounded and closed and the other is open. The contents of hard capsules are usually in solid form (powder or granules).

Hard capsule shells are classically made of gelatin, the consistency of which may be adjusted by the addition of a plasticizer such as glycerol or sorbitol.

Gelatin is a translucent, almost colorless, brittle (when dry), flavorless material, derived from collagen obtained from various animal by-products, mainly pig skin, bovine skin, and bones.

After dissolution in hot water and cooling, gelatin forms a semi-solid colloidal gel which has many advantages for the preparation of capsules. Gelatin has rapid gelling ability, excellent film forming properties, and ability to impart oxygen impermeability. Films formed from plasticized gelatin set very quickly and have high wet film strength. They are also very elastic with good clarity. Plasticized gelatin also has a relatively low viscosity, even when used at high solids concentrations. In addition, when gelatin is in the presence of water at room temperature, it swells but does not go into solution until heat is applied.

For many years, gelatin had good press. However, following the emergence of bovine spongiform encephalitis, the use of gelatin in edible preparations has become very controversial.

Moreover, the use of gelatin is not compatible with certain beliefs, or religious practices. Some vegetarians and vegans notably refuse to consume any products derived from animals and consequently boycott all edible products containing gelatin. Gelatin also has the disadvantages of batch property variations, limited availability and high cost.

Because of these shortcomings, those industries where the need for gelatin is greatest, have long sought means for getting rid of gelatin, in favor of 100% plant-based solutions.

To this end, various alternatives have been proposed, but these alternatives lacked consistency from the industrial point of view, so that they were never developed further.

Hydroxypropyl methylcellulose (HPMC), pullulan, or carrageenan for instance, which are vegetarian-acceptable alternatives to gelatin, are way too expensive to produce, even more than gelatin.

Starch-based formulations have also been employed. However, the films formed thereof lack transparency and stability. After several months, the strength, the flexibility and the plasticity of the films obtained therefrom decrease. This results in parallel, in an increase of their friability and opacity. Also, for the preparation of capsule shells, the time required for the step of dipping is relatively long with those formulations (20 seconds compared to 1 or 2 seconds for gelatin solution).

Indeed, a useful gelatin replacer should provide properties equivalent to those of the gelatin which it is replacing for a particular application; and this for a reasonable price. For capsules manufacture, the capsules should possess the properties of good wet and dry film strength, suitable solubility parameters, temperature and pressure seal ability, film clarity, film flexibility, edibility, inertness to drugs or other materials to be encapsulated, and rapid setting from a hot liquid to form a gel.

Recently, in patent application PCT/EP2016/068743, the inventors developed suitable composition for the preparation of both hard and soft capsules, characterized by the fact that it comprises isosorbide and a plasticizer. The capsules obtained thereof had good stability and transparency. However, there was still a need to improve such formulation.

PRESENTATION OF THE INVENTION

It was thus an object of the invention to provide film-forming compositions for hard capsule shells based on starchy material making partial replacement, ideally total replacement, of gelatin in these compositions possible.

In particular, it was an object of the present invention to provide film-forming compositions that are suitable for the preparation of articles such as edible hard capsule shells.

It was another object of the invention to provide film-forming compositions using bio-based materials, preferably excluding material of animal origin, which are easy to manufacture and easy to handle, and which do not involve excessive costs for their preparation and use.

The inventors succeeded in remedying the drawbacks of gelatin-free and starch-based compositions of the prior art, by developing particular film-forming compositions, which comprise starch, gellan gum, isosorbide, sorbitol and glycerol.

In the film-forming compositions of the invention, the starch likely acts as a film-forming agent, whereas the gellan gum acts as a gelling agent.

As for the isosorbide, it is not clearly understood how it acts in these compositions. In any case, it seems clear that isosorbide positively impacts the plasticizer's effects, i.e. the effect of glycerol and sorbitol.

The film-forming compositions of the invention do not require the use of gelatin. Partial and even total replacement of gelatin is thus possible for the preparation of articles such as capsule shells.

The film-forming compositions of the invention can advantageously be entirely composed of materials of natural origin, in particular and advantageously of non-animal origin.

Contrary to the film-forming compositions of prior art, these compositions allow the preparation of hard capsule shells with excellent properties, notably with respect to mechanical resistance, solubility, transparency, flexibility, drought resistance, moisture proof and disintegration. Also, these film-forming compositions are easy to use: the capsules manufacturers can replace their classic gelatin compositions by the film-forming compositions of the invention by using the equipment which is already in their possession; and this, without requiring significant changes in the process settings.

The capsule shells manufactured by using the film-forming composition of the invention can comply with important application of the cosmetic, pharmaceutical, food, animal feed and in between industries. As a result, the film-forming compositions of the invention can be used for de preparation of hard capsule shells intended for many applications.

BRIEF DESCRIPTION OF THE INVENTION

Therefore, a first aspect of the invention relates to a film-forming composition comprising hydrolyzed starch, gellan gum, isosorbide, sorbitol and glycerol.

According to a second aspect, the invention relates to a capsule shell comprising hydrolyzed starch, gellan gum, isosorbide, sorbitol and glycerol.

According to a third aspect, the invention relates to hard capsules comprising a hard capsule shell according to the invention.

According to a fourth aspect, the invention relates to a method for the manufacture of hard capsule shells, comprising a step of molding a film-forming composition of the invention.

DETAILED DESCRIPTION OF THE INVENTION

Film-forming Composition

Figure 1A:
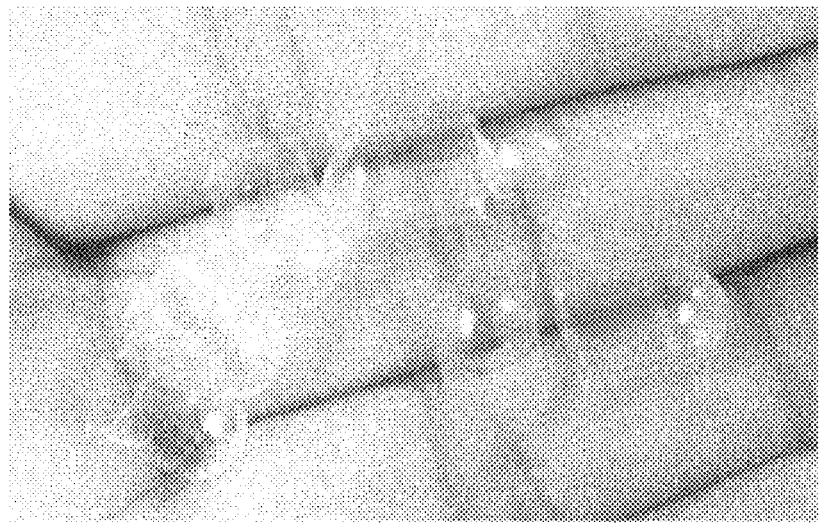
FIGS. 1A-1C show photographs of the capsules obtained.

The film-forming compositions of the invention are characterized by the fact that they comprise hydrolyzed starch, gellan gum, isosorbide, sorbitol and glycerol.

It is reminded herein that the expression "film-forming composition" classically refers to a composition comprising at least one polymer (film-forming agent), said polymer being able to form an essentially continuous film in the presence of a solvent, water in particular. In the instant invention, film-forming compositions are in particular starchy film-forming compositions, i.e. using a starch, as main film-forming agent, in particular a hydrolyzed starch.

It is also reminded that the expression "starch" classically refers to the starch isolated from any suitable botanical source, by any technique well known to those skilled in the art. Isolated starch typically contains no more than 3% of impurities; said percentage being expressed in dry weight of impurities with respect to the total dry weight of isolated starch. These impurities typically comprise proteins, colloidal matters and fibrous residues. Suitable botanical sources include for instance legumes, cereals, and tubers.

In this regard, the starch useful to the invention is preferably a pea starch, a maize starch, a tapioca starch or a mixture thereof, preferably a pea starch.

Preferably, the hydrolyzed starch of the invention is derived from a native starch exhibiting an amylose content chosen within the range of from 25 to 45%, preferably of from 30 to 45%, preferably of from 35 and 40%; these percentages being expressed in dry weight of amylose with respect to the total dry weight of said native starch from which it is derived.

The hydrolyzed starch useful to the invention might also have undergone other physical and/or chemical modifications, as long as it does not interfere with the desired properties of said hydrolyzed starch. Examples of chemical modification are alkylation and cross-linking. Physical modifications preferably comprise gelatinization, and pre-gelatinization.

Preferably, the hydrolyzed starch useful to the invention is also alkylated, preferably hydroxypropylated.

In this case, the hydrolyzed hydroxypropylated starch useful to the invention generally has a content of hydroxypropyl groups of between 1 and 50%, even of between 1 and 15%, even of between 5 and 9%, for instance of between 6 and 8%; said percentages being expressed in dry weight of hydroxypropyl groups with respect to the total dry weight of hydroxypropylated hydrolyzed starch, and determined by Proton nuclear magnetic resonance (proton NMR), for instance according to the standards EN ISO 11543:2002 F.

The hydrolyzed starch useful to the invention, in particular the hydrolyzed alkylated starch useful to the invention, preferably has a weight average molecular weight of between 20 and 2 000 kDa, preferably of between 100 and 1 000 kDa, for instance of between 200 and 800 kDa, for instance of between 200 and 500 kDa, or of between 200 and 400 kDa; said weight average molecular weight being determined by HPSEC-MALLS (High Performance Size Exclusion Chromatography coupled on-line with Multiple Angle Laser Light Scattering).

Suitable hydrolyzed starches are commercially available. Particularly preferred hydrolyzed starches are hydroxypropylated hydrolyzed starch marketed under the brand LYCOAT® by ROQUETTE.

Preferably, the gellan gum useful to the invention is acyl-gellan gum, preferably low acyl-gellan gum.

In a particular preferred embodiment of the invention, the film-forming compositions of the invention are composed of:

50 to 98% of hydrolyzed starch, preferably 70 to 95%, for instance 80 to 90%;

0.5 to 10% of gellan gum, preferably 1 to 8%, preferably 1 to 5%, for instance 1 to 3%;

0.5 to 10% of isosorbide, preferably 1 to 8%, preferably 1 to 5%, for instance 1 to 3%;

0.5 to 10% of sorbitol, preferably 1 to 8%, preferably 1 to 6%, for instance 2 to 5%;

0.5 to 10% of glycerol, preferably 1 to 8%, preferably 1 to 6%, for instance 2 to 5%;

optionally 0 to 0.50% of a buffering agent, preferably potassium salts, for instance selected from among KCl, $K_3PO_4$, $KH_2PO_4$, potassium citrate, preferably KCl, preferably 0.01 to 0.50%, preferably 0.05 to 0.40%, for instance 0.10 to 0.30%;

optionally 0 to 10% of other ingredients, preferably 0 to 5%, typically 0 to 3% or even 0 to 1%;

said percentages being expressed in dry weight of ingredient with respect to the total dry weight of said film-forming composition, and their sum being equal to 100%.

The film-forming compositions of the invention can indeed comprise other ingredients, as long as it does not interfere with the desired properties of said film-forming compositions. Such other ingredients can be for instance: surface-active substances, opaque fillers, conservatives, antimicrobial agents, sweeteners, flavouring substances, colors, brightening agents, disintegrating agents, glidants, lubricants, substances capable of modifying the disintegration behavior of the film in the gastrointestinal tract.

Such other ingredient can also be selected from hydrocolloids, either alone or in combination, other than the hydrolyzed starch and the gellan gum of the invention.

Such other hydrocolloids typically are polysaccharides, proteins, gelatin, and synthetic polymers such as hydroxypropylmethylcellulose, hydroxypropylcellulose, polyvinyl alcohol. It is for instance selected from carrageenans, alginates, pullullans, glucomannans, for instance Konjac glucomannans, xanthans, tara gums, pectins, arabic gums or mixtures thereof.

Of course, if gelatin is used, it preferably represents no more than 50% of the film-forming composition, preferably no more than 30%, preferably no more than 10%, preferably no more than 5%, preferably no more than 1%; these percentages being expressed in dry weight of gelatin with respect to the total dry weight of the film-forming composition. Even more preferably, the film-forming composition of the invention is free of gelatin.

Such other ingredients can also be selected from plasticizers other than glycerol and sorbitol. Such other plasticizers can for instance be selected from trehalose, polyethylene glycol, triethyl citrate, polysorbate, Carnauba wax, hydrogenated castor oil, or from mixtures thereof.

Preferably, the film-forming compositions of the invention are essentially composed of, or even entirely composed of ingredients of natural origin, preferably of non-animal origin, preferably of plant-origin.

Preferably, the film-forming compositions of the invention are composed of edible ingredients.

Preferably, the film-forming compositions of the invention are capable of forming a film which is soluble in water at a temperature chosen from 4 to 50° C., even from 20 to 40° C., for instance at room temperature (chosen from 20 to 25° C.), or at 37.5° C.

To be able to form a film, the ingredients of the film-forming composition must be dissolved in a suitable solvent, just prior to its use. This can be achieved by simply mixing the ingredients with a solvent, under heating if necessary, for instance at about 90° C. Preferably, the solvent is water.

Accordingly, the film-forming composition of the invention can be in the liquid form, in particular in the form of a solution, preferably in the aqueous form.

In general, this liquid film-forming composition has a dry matter content by weight of between 10 and 70%, even of between 20 and 60%, even of between 20 and 50%, even of between 25 and 45%, for instance of between 25 and 35%.

Film-forming compositions in the powdery form are also covered in the instant invention. These typically are "ready-to-use" powdery compositions. In the latter case, the use of the powdery composition classically only requires the addition of a solvent, preferably water, and solubilization of said powdery composition in said solvent.

In the case where the film-forming composition is in the powdery form, it can be prepared by simply mixing the various powdery ingredients composing it. However, it can advantageously be in the form of a spray-dried powder. In the latter case, the film-forming composition is advantageously prepared first by dissolving the ingredients in any suitable solvent, preferably water. The liquid composition thus obtained is then spray-dried so as to obtain a powder. This spray-dried form has the advantage of being very easy to use, for instance by the capsules manufacturers: dissolution of this powder is easier to achieve, at lower temperatures, as compared to simple physical mixtures.

Hard Capsule Shells and Methods for Their Preparation

The film-forming compositions of the invention are capable of forming edible water-soluble films or gels, more or less rigid, which are useful for the manufacture of hard capsule shells.

The invention thus also relates to a hard capsule shell comprising hydrolyzed starch, gellan gum, isosorbide, sorbitol and glycerol.

Preferably, the composition of the dry matter of the capsule shell is as described before, for the film-forming composition according to the invention.

The solid content of the hard capsule shell is preferably higher than 80%, even higher than 85%, usually of between 85 and 95%.

Preferably, the hard capsule shells of the invention are soluble in water at a temperature chosen from 4 to 50° C., even from 20 to 40° C., for instance at room temperature (chosen from 20 to 25° C.), or at 37.5° C.

Preferably, the capsule shells of the invention are edible.

The instant invention also covers hard capsules comprising such capsule shells.

The invention also relates to a method for the manufacture of hard capsule shells, comprising a step of molding a film-forming composition according to the invention.

The hard capsule shells of the invention can be obtained more precisely according to a method comprising the steps of:
- (a) providing a film-forming composition according to the invention in the liquid form;
- (b) molding the capsule shells with the composition obtained in step (a);
- (c) drying the molded composition obtained in step (b);
- (d) recovering the capsule shells thus obtained.

Step (b) may in particular be performed by dipping pins into the film-forming composition.

Preferably, drying step (c) is performed by heating at a temperature of less than 100° C., preferably of less than 80° C., preferably of between 30 and 50° C., for instance of between 35 and 45° C.

The film-forming compositions of the invention are thus really simple to prepare and to handle. Like for gelatin, solubilizing the ingredients, heating at moderate temperatures, and drying is sufficient to obtain the desired product.

Unless otherwise specified, it should be understood in the instant invention that the expression "between X and Y" excludes the recited limits, whereas the expression "chosen within the range of from X to Y" includes the recited limits.

It is further understood that the "dry weight of an ingredient" excludes the water eventually intrinsically present in the ingredient in its powdery state.

The following Examples serve to illustrate the invention and should by no means be construed so as to limit the scope of the invention.

EXAMPLES

In the following Examples, for convenient reading, the tests according to the invention are identified with the reference "IN-X", whereas the comparative tests are identified with the reference "CP-X".

1. Preparation of Hard Capsule Shells at Pilote Scale

In the following tests, film-forming compositions were prepared as follow.

Glycerol (when present), isosorbide (when present) and KCl were dissolved in 265 g deionized water. The starchy material, sorbitol (when present), and gellan gum or κ-carrageenan were premixed firstly and were then added to the aqueous solution. The mixture was stirred for 20 minutes using mechanical stirring at 500 rpm. The mixture was then heated at 90° C. for 1 hour using water bath for solubilizing all ingredients. The solution was then kept at 70° C. for 3 hours in order to eliminate the bubbles and then at 60° C. for 1 hour before dipping (viscosity≈300 cps). The mold was preheated at 36° C. before using. After dipping, the mold was dried at 36° C. and 30% RH for 50 minutes. After demolding, the hard capsules were reassembled.

Results obtained are presented in Table 1.

TABLE 1

|  | IN-1 | CP-1 | CP-2 | CP-3 | CP-4 | CP-5 |
| --- | --- | --- | --- | --- | --- | --- |
| Ingredients |  |  |  |  |  |  |
| Hydrolyzed hydroxypropylated starch* | 87.1% |  | 87.1% | 87.1% | 87.1% | 87.1% |
| Hydroxypropylated starch |  | 87.1% |  |  |  |  |
| Low acyl gellan gum | 1.9% | 1.9% |  | 1.9% | 1.9% | 1.9% |
| κ-carrageenan |  |  | 1.9% |  |  |  |
| Isosorbide | 2.2% | 2.2% | 2.2% | 2.2% | 2.2% |  |
| Sorbitol | 4.3% | 4.3% | 4.3% |  | 8.6% | 5.4% |
| Glycerol | 4.3% | 4.3% | 4.3% | 8.6% |  | 5.4% |
| KCl | 0.2% | 0.2% | 0.2% | 0.2% | 0.2% | 0.2% |
| Solids content | 29% | 29% | 29% | 29% | 29% | 29% |
| Results | Transparency: + Physical properties: + Stability: + | Impossible to handle | Transparency: + Physical properties: + Stability: +/− | Transparency: + Physical properties: − Stability: nd | Transparency: + Physical properties: + Stability: +/− | Transparency: + Physical properties: + Stability: − |

*hydrolyzed hydroxypropylated pea starch, having hydroxypropyl content of 7%; weight average molecular weight of 330 kDa (LYCOAT ® RS 780, Roquette Frères)
nd: not determined.
In this table, the amounts of ingredients are expressed in dry weight of ingredient with respect to the total dry weight of the composition.

Composition CP-1 (using a non-hydrolyzed starchy material) was impossible to handle so that the Applicant were not even able to obtain capsules thereof.

Compositions CP-2 (using κ-carrageenan as a gelling agent instead of gellan gum), and CP-4 (without glycerol) allowed the obtaining of transparent capsules with good physical properties. However those hard capsules were not as stable as the ones obtained from composition IN-1 according to the invention. Hard capsules obtained from composition CP-2 and CP-4 became brittle over time, due to water losses.

Composition CP-3 (without sorbitol) allowed the obtaining of transparent capsules. However its physical properties were not suitable for use in hard capsules, as the films obtained thereof were too soft.

Composition CP-5 (without isosorbide) allowed the obtaining of transparent capsules with good physical properties. However the hard capsules were not stable at all: they became brittle and lost their transparency very quickly.

2. Preparation of Hard Capsule Shells at Industrial Scale

Composition IN-1 was tested on industrial equipment for the manufacture of hard capsules.

Figure 1B:
Figure 1C:
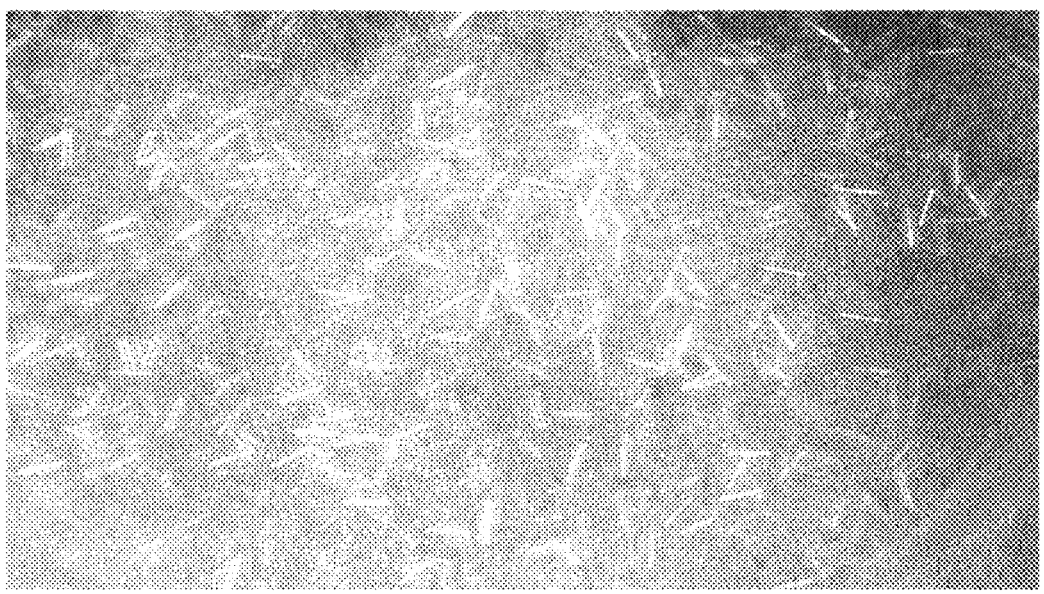

Photographs of the capsules obtained are presented in FIGS. 1A-1C.

Great quantities of hard capsule shells were obtained, with good transparency, physical properties and stability. This allowed the Applicant to confirm that the compositions according to the invention are suitable for use at industrial scale.

The invention claimed is:

1. A film-forming composition in liquid aqueous form, comprising hydrolyzed starch, gellan gum, isosorbide, sorbitol and glycerol, having a dry matter content by weight of between 10 and 70%.

2. The film-forming composition of claim 1, wherein the hydrolyzed starch is alkylated.

3. The film-forming composition of claim 2, wherein the hydrolyzed starch is hydroxypropylated.

4. The film-forming composition of claim 1, wherein said film-forming composition is essentially composed of ingredients of natural origin.

5. A hard capsule shell comprising hydrolyzed starch, gellan gum, isosorbide, sorbitol and glycerol.

6. A hard capsule comprising a hard capsule shell according to claim 5.

7. A method for the manufacture of hard capsule shells, comprising a step of molding a film-forming composition such as defined in 1.

* * * * *